United States Patent [19]

Shoesmith

[11] Plant 5,144

[45] Nov. 22, 1983

[54] CHRYSANTHEMUM NAMED TREASURE

[75] Inventor: Leonard H. Shoesmith, Westfield-Woking, England

[73] Assignee: Pan-American Plant Company, Parrish, Fla.

[21] Appl. No.: 359,892

[22] Filed: Mar. 19, 1982

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Chas. W. Rummler

[57] ABSTRACT

A new variety of chrysanthemum plant having large, bright, clear yellow blooms of incurve standard type with long, strong stems, when disbudded, and having a vigorous, upright and rapid growth habit, and a nine-week response for year round flowering.

1 Drawing Figure

BACKGROUND OF THE NEW PLANT

This new chrysanthemum cultivar originated as a seedling of unknown parentage grown in greenhouse at West Chicago, Ill., from seeds selected by me from plants growing in a field of randomly-hybridized chrysanthemum varieties produced with the object of discovering plants of unusual character and color and having commercial market merit. This plant was selected for propagation and test because of its clear bright yellow color and large blooms borne on tall, strong stems. Propagation of this plant through successive generations, by means of cuttings, at West Chicago, Ill., has shown the novel characteristics of this cultivar to hold true from generation to generation and to appear to be firmly fixed. Commercial production of this variety, by cuttings, is now being done at Parrish, Fla.

DESCRIPTION OF THE DRAWINGS

This new chrysanthemum cultivar is illustrated by the accompanying drawing, which shows a hand painted photographic rendition of a bloom of the new variety showing its true color.

DESCRIPTION OF THE NEW PLANT

The following is a detailed description of this new variety of chrysanthemum with color descriptions according to The R.H.S. Colour Chart published by The Royal Horticultural Society of London, England.

THE PLANT

Origin: Seedling.
Parentage: Unknown.
Classification:
- *Botanic.*—Chrysanthemum Morifolium.
- *Commercial.*—Greenhouse cut flower.

Form: Incurve standard.
Height: Tall; variable from 3 to 6 feet.
Growth: Strong, upright and vigorous.
Growth rate: Rapid.
Foliage: Abundant in quantity.
- *Leaf size.*—To about 12 cm. long and about 7 cm. wide.
- *Leaf shape.*—Ovate with cleft margins.
- *Texture.*—Leathery.
- *Ribs and veins.*—Pinnate.
- *Color.*—Upper side — 147A. Under side — 147B.

- *Petioles.*—Length — To about 5 cm.
- *Leaflets.*—None.

THE BUD

Form: Globular.
Size: Variable in both diameter and length.
Opening rate: Varies with temperature.
Color:
- *When phyllaries first divide.*—6B.
- *When petals begin to unfurl.*—6B.

Phyllaries:
- *Number.*—About 35.
- *Shape.*—Lanceolate.
- *Color.*—147C.

Flower stem:
- *Length.*—10 to 14 cm.
- *Character.*—Rigid.
- *Aspect.*—Pubescent.
- *Color.*—147D.

THE FLOWER

Blooming habit: Recurrent.
Blooming characteristics: 9-week response at any time of the year.
Size of bloom: Very large.
- *Diameter.*—10 to about 13 cm.
- *Depth.*—Flat.

Borne: Singly when disbudded; otherwise in raceme cluster.
Form: A completely double composite inflorescence borne on a receptacle surrounded by an involucre of bracts.
Shape:
- *When bloom first opens.*—Cup-shaped.
- *When bloom matures.*—Flattened.

Petalage: Many ray and disc florets.
- *Phyllaries.*—About 35.
- *Arrangement.*—Imbricated.
- *Form.*—Incurved with rounded apex and entire margins.
- *Texture.*—Soft.
- *Appearance.*—Satiny.
- *Color.*—Inside of florets — 6B. Outside of florets — 6C.

Flower stem:
- *Character.*—Strong and upright.
- *Color.*—147D.

Fragrance: Typical chrysanthemum.

Persistence: Flower hangs on and dries.
Lasting quality:
*On plant.*—3 to 4 weeks.
*As cut flower.*—2 to 3 weeks.

REPRODUCTIVE ORGANS

Stamens: 5 in number in syngenesious arrangement.
*Anthers.*—Size — Insignificant. Color — Yellow.
*Filaments.*—Length — Insignificant. Color — Yellow.
*Pollen.*—Color — Yellow.
Pistils:
*Number.*—One for each floret.
*Styles.*—Length and color — Insignificant.
Stigmas:
*Color.*—Insignificant.
Character of ovaries.—Inferior bicarpellate.

This plant is an incurved standard chrysanthemum for year round flowering and is particularly distinguished by its bright, clear yellow coloration. It is a vigorous plant with long, strong stems and has a subsantially uniform nine-week response which allows it to be grown with the "Bounties" but its color and excellent incurve form are improvements on "Golden Bounty" (U.S. Plant Pat. No. 4,482).

I claim:

1. A new and distinct chrysanthemum cultivar, substantially as herein shown and described, characterized by its unique bright, clear yellow, incurve, standard bloom. This plant is vigorous with strong stems and capability for year round flowering with a substantially constant nine-week response.

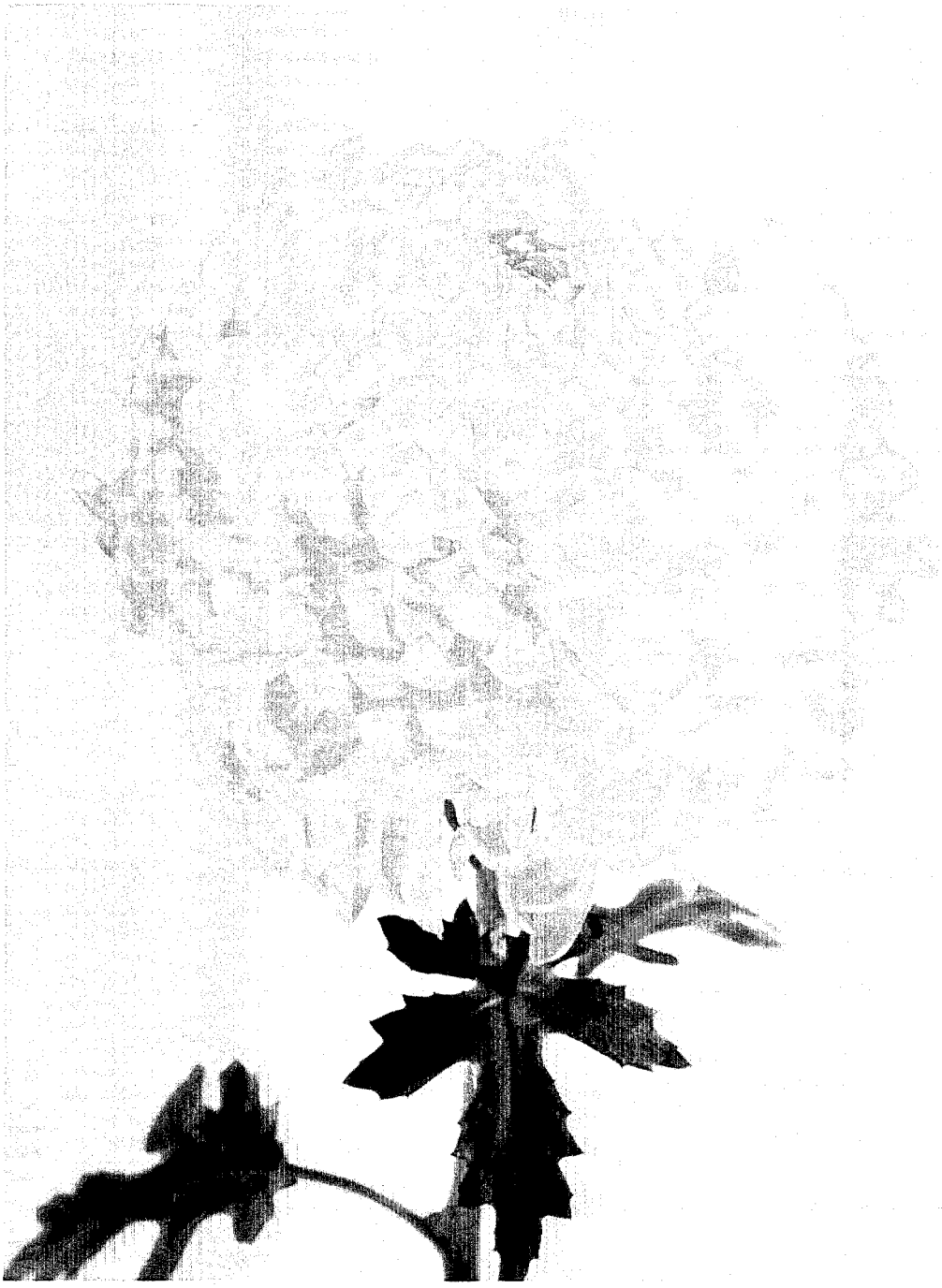

* * * * *